United States Patent
Shifrine

(10) Patent No.: US 8,679,507 B2
(45) Date of Patent: Mar. 25, 2014

(54) TESTOSTERONE OLFACTION

(71) Applicant: Moshe Shifrine, Santa Fe, NM (US)

(72) Inventor: Moshe Shifrine, Santa Fe, NM (US)

( * ) Notice: Subject to any disclaimer, the term of this patent is extended or adjusted under 35 U.S.C. 154(b) by 0 days.

(21) Appl. No.: 13/864,520

(22) Filed: Apr. 17, 2013

(65) Prior Publication Data

US 2013/0295140 A1    Nov. 7, 2013

Related U.S. Application Data

(60) Provisional application No. 61/641,358, filed on May 2, 2012, provisional application No. 61/734,551, filed on Dec. 7, 2012.

(51) Int. Cl.
*A61K 36/06* (2006.01)

(52) U.S. Cl.
USPC .................................................. 424/195.15

(58) Field of Classification Search
None
See application file for complete search history.

(56) References Cited

U.S. PATENT DOCUMENTS

| 2004/0009143 A1* | 1/2004 | Golz-Berner et al. ........... 424/74 |
| 2012/0039927 A1* | 2/2012 | Morgan ................... 424/195.15 |

FOREIGN PATENT DOCUMENTS

CN    101313920 A   * 12/2008

OTHER PUBLICATIONS

Buster, Transdermal menopausal hormone therapy: delivery through skin changes the rules. Expert opinion on pharmacotherapy, (Jun. 2010) vol. 11, No. 9, pp. 1489-1499.*

* cited by examiner

*Primary Examiner* — Qiuwen Mi
(74) *Attorney, Agent, or Firm* — Kohn & Associates, PLLC

(57) ABSTRACT

A composition of an olfactory stimulus mechanism for stimulating the production of testosterone. A method of increasing the level of testosterone in an individual by smelling the truffle extract, causing androgens in the truffle extract to attach to the olfactory bulb in the individual, and inducing testosterone production. A method of preventing the onset of Alzheimer's disease in an individual by the individual smelling the truffle extract, and inducing testosterone production in the individual. A method of treating symptoms of menopause in a woman by the woman smelling the truffle extract, and inducing testosterone production in the woman. A method of treating andropause in a man by a man smelling the truffle extract, and inducing testosterone production in the man.

3 Claims, No Drawings

TESTOSTERONE OLFACTION

BACKGROUND OF THE INVENTION

1. Technical Field

The present invention relates to hormone treatments. More specifically, the present invention relates to testosterone treatments.

2. Background Art

Testosterone is a compound needed and produced by the body in both men and women for several different functions. It is needed for the development and maintenance of sex organs and characteristics, as well as for muscle growth, bone development, and bone maintenance. The production of testosterone is regulated by the brain through the release of hormones. Testosterone is produced in the testes, 95% and 5% in the adrenals. To stimulate its production the hypothalamus releases to the pituitary gland a gonadotropin-releasing hormone (GnRH), which, in turn, causes the pituitary to produce a follicle-stimulating hormone (FSH) and a luteinizing hormone (LH) collectively known as gonadotropins. LH is released into the blood stream and travels to the testes to trigger the production of testosterone from cholesterol (!). When the testosterone level gets too high the pituitary slows the release of LH to slow it down. The actual testosterone production occurs in the Leydig cells in the testes and adrenals in men and also in women production occurs in the ovaries and adrenals. Healthy young men produce about 6 milligrams of testosterone per day and healthy women produce 0.3 mg of testosterone per day ($\frac{1}{20}^{th}$ of what men produce).

While age can naturally decrease testosterone levels, many individuals suffer from lower than normal levels of testosterone. Low levels of testosterone can be caused by hypogonadism (a problem with the organs that produce testosterone, i.e. the ovaries or testes), secondary hypogonadism (a problem with regulation of testosterone), or tertiary hypogonadism (a problem with the hypothalamus). Each of these problems can be caused by a variety of factors, including aging, injury, disease, cancer therapies such as chemotherapy and radiation therapy, chromosomal abnormalities, drug use, and obesity. In particular, secondary and tertiary hypogonadism are caused by diseases that affect the hypothalamic-pituitary-gonadal axis (i.e. the system of the hypothalamus, pituitary gland, and gonads). The hypothalamus produces gonadotropin-releasing hormone (GnRH), the anterior portion of the pituitary gland produces luteinizing hormone (LH) and follicle-stimulating hormone (FSH), and the gonads produce testosterone.

Low levels of testosterone, commensurate with high levels of cortisol, are also associated with stress, depression and other psychological disorders. This occurs through interconnections linking the components of the body in stress apparatus i.e. the nerves, hormonal glands (HPA axis) and the immune system. Other symptoms of low testosterone in men include decreased libido, infertility, erectile dysfunction, loss of hair, decreased muscle mass, osteoporosis, and, in women, include hot flashes, irritability, decreased libido, sleep disturbances, loss of muscle mass, osteoporosis, and loss of body hair. To make matters worse for aging men, many conventional antidepressant medications suppress testosterone production and thus libido. As women go through menopause, they also have many of these problems because of lower levels of testosterone.

Treatments for low testosterone currently include hormone replacement therapy (HRT or TRT—testosterone replacement therapy). Testosterone can be given to men as an intramuscular injection, patch or gel placed on the skin, or a putty applied to the gums of the mouth. Some experts suggest that testosterone replacement therapy might reduce the need for the antidepressant medications entirely. Unfortunately, there is no current treatment available for women. Some women resort to using patches available for men and cutting them to a size more appropriate of a dose for women, but this has questionable accuracy and safety.

ANDROGEL® (Abbott Laboratories) is one product on the market for TRT for men that contains synthetic testosterone, and when applied to the skin, it increases the concentration of testosterone. The dose used is 100 times as what is present in the blood. The use of ANDROGEL® can produce unwanted side effects, such as causing irritation to the skin due to the carrier used which includes many chemicals to facilitate penetration through the skin. It is also an expensive drug.

Olfaction, the sense of smell, is critical for the survival of almost all creatures. Humans are able to distinguish over 10,000 different odor molecules. With every inhalation, currents of air swirl through the nostrils over the bony turbinates in the nose that contain receptors in the olfactory epithelium. The cilia projecting from the olfactory knob contain receptors for odorants. The cilia project from the knob directly into the atmosphere. The interaction of the right molecule with the right receptor causes a structural transformation of the receptor, which gives rise to an electrical signal to the olfactory bulb and thence to the areas in the limbic brain that perceive it as the original smell.

In 2000 Shinohara, et al. published a study on the effect of androstenol on the pulsating secretion of the luteinizing hormone (LH) in human females. The subjects, female college students, had their upper lip exposed to androstenol and their pulsating frequency of LH was measured. The frequency of the pulse in the follicular phase was decreased. This is a direct proof that sniffing androstenol affects the LH pulse. In a subsequent study (Shinohara, et al. 2001) it was determined that axillary pheromones (putatively androstenol) modulated the LH of humans.

Preti, et al. (2003) showed that male axillary extracts (underarm secretions) affect the pulsating secretion of LH and the mood of the women participants in this experiment.

From these studies, it is evident that presenting human hormones through the olfactory system elicits a physiologic response.

Another study (unpublished work by Shifrine) showed that pigs fed cultured truffle powder (i.e. French truffles grown in hydroponics and on grain) in their feed exhibited improved feed efficiency, significantly lowered feed consumption, significantly lowered fat, and increased leanness of carcasses. The very low dose of 1 gram dried powdered cultured truffle per ton of feed suggested that the effect of the truffle was due through inhalation and not ingestion. This suggests a "testosterone response". However, at the time of this study, testosterone had not been reported in scientific literature to be present in truffles. Androstenol, shown to be contained in truffles, on the other hand was isolated from pig testes by Prelog & Ruziaka (1944). It was later discovered in truffles and offered as an explanation for the ability of pigs to detect this hypogeous mushroom (Claus et al., 1981).

In 2006, Applicant discovered that, in addition to androstenol, the truffle culture produces testosterone, which might explain the 'testosterone effect' in pigs, and the reason truffles are reputed to have aphrodisiac potential. At the concentration of 1.7 µg of testosterone in a gram of dry weight of truffles (truffle powder, from truffles grown on grain), which is equivalent to ca. $6 \times 10^{15}$ molecules, there are ample molecules to cover all androgen receptors in the nose. Since pigs are the best experimental animals for humans (Simon and Maibach, 2000) it is reasonable to extrapolate the data from the pig study to humans.

Therefore, there remains a need for a safe and effective method of increasing testosterone in both men and women who suffer from low levels of testosterone.

SUMMARY OF THE INVENTION

The present invention provides for a composition that stimulates the production of testosterone through olfaction.

The present invention provides for a method of increasing the level of testosterone in an individual by smelling the truffle extract, causing androgens in the truffle extract to attach to the olfactory bulb in the individual, and inducing testosterone production.

The present invention provides for a method of preventing the onset of Alzheimer's disease in an individual by the individual smelling the truffle extract, and inducing testosterone production in the individual.

The present invention provides for a method of treating symptoms of menopause in a woman by the woman smelling the truffle extract, and inducing testosterone production in the woman.

The present invention also provides for a method of treating andropause in a man by a man smelling the truffle extract, and inducing testosterone production in the man.

DETAILED DESCRIPTION OF THE INVENTION

The present invention provides generally for a composition that stimulates the production of testosterone through transmucosal administration (administration via any mucosal surface of the body, and preferably by olfaction) and a method of treating low testosterone levels in both men and women with the olfaction. This is a unique method that is used as a testosterone replacement therapy.

Preferably, the composition of the present invention is a truffle extract that provides an olfactory stimulus. Truffles are mushrooms, and more specifically, the fruiting bodies of subterranean mushrooms. Truffles are generally found near tree roots of beech, poplar, oak, birch, and pine trees. Any type of truffle can be used to obtain the truffle extract, such as, but not limited to, white truffle (*Tuber magnatum, Tuber magnatum pico,* or *Tuber borchii*), black truffle (*Tuber melanosporum*), black summer or burgundy truffle (*Tuber aestivum/uncinatum*), *Tuber macrosporum, Tuber oregonense, Tuber gibbosum,* and *Tuber lyoni*. The truffles are preferably cultured truffles, but wild truffles can also be used. Cultured truffles (in particular *Tuber melanosporum*) have been found to be identical to wild truffles by DNA analysis. The extract can also be derived from truffle mycelium grown in vitro.

Truffles naturally contain testosterone, and the present invention provides for an extract from a truffle that can be smelled by an individual. One gram of dry weight of truffles contains 1.7 µg of testosterone, which is equivalent to ca. $6 \times 10^{15}$ molecules. There are ample molecules to cover all androgen receptors in the nose. Since pigs are the best experimental animals for humans (Simon and Maibach, 2000) it is reasonable to extrapolate the data from the pig study described above to humans. Based on the finding of testosterone, in the cultured truffles, the present invention is based on the finding that cultured truffle testosterone scent activates androgenic receptors in the brain of men and women with subsequent initiation of its anabolic pathway.

Preferably, the composition is prepared by harvesting truffles, drying, and then milling the truffles to a fine powder. The fine powder can then be combined with any appropriate excipients as further described below, or be used in nutraceutical formulations. A tincture extract of 0.5 g to 1 g or more of truffles can be administered; however, even smaller amounts such as picograms or less of the truffles can be used.

Alternatively, any other composition that can provide olfaction of testosterone can be used. For example, the composition can be pollen of the pine tree *Pinus silvestris* that contains testosterone. While the truffle extract is further described in the methods herein, it should be understood that one skilled in the art can use any other composition that provides olfaction of testosterone in the same manner.

The composition can be in the form of a pharmaceutical composition or a nutraceutical composition. The pharmaceutical or nutraceutical composition is preferably a topical composition for application to the skin. The composition can be applied to any part of the skin, such as, but not limited to, the wrist or the upper lip, much like a perfume. The truffle extract can be added to a pharmaceutically/nutraceutically acceptable carrier of alcohol or oil that still allows for the scent of the truffle to be detected. Preferably, the carrier is alcohol because it evaporates easily from the skin; however, any other appropriate carrier (such as a wax or a cream) can be used. Furthermore, while not preferred in combination with the alcohol carrier, any other pharmaceutical or nutraceutical excipients can also be used where appropriate. The amount of truffle extract in a pharmaceutically or nutraceutically effective amount can be determined by one skilled in the art but generally is in an amount to increase the levels of testosterone in an individual and return the testosterone levels to a normal level.

The composition is administered to an individual, preferably a mammal, such as, but not limited to, humans and pigs. One preferred time of administration is in the evening or night before the individual goes to sleep. Testosterone has a circadian rhythm so that it is highest in the morning and lowest at night. Therefore, administration of the composition during the lowest natural levels of testosterone can have a greater effect on the individual. The individual using the composition can be any age, but it is preferable to use the compound at an age when testosterone levels are lower than normal. For example, at ages 50 to 60, testosterone levels can be approximately half of the levels at age 13 (the age at which testosterone levels are generally highest). Use at the ages of 50 to 60 can be beneficial for the prevention of libido as well as Alzheimer's disease. Alzheimer's disease generally has a 15-year period between the onset and the development of symptoms, and therefore, early administration of the composition before any symptoms can help in the prevention of Alzheimer's disease (also further described below).

The composition of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The doses can be single doses or multiple doses over a period of several days. The treatment generally has a length proportional to the length of the disease process and drug effectiveness and the patient species being treated.

The present invention provides for a method of initiating the normal production of testosterone in an individual by smelling the composition (i.e. truffle extract). Essentially, the levels of testosterone are increased in the individual. Smelling the truffle induces testosterone production in the individual when androgenic receptors in the brain are activated. Androgens contained in the truffle extract travel to the nose upon smelling and attach to androgen receptors in the olfactory bulb. Preferably, the application is performed by applying to the skin before an individual goes to sleep because testosterone levels are at their lowest at this time.

By smelling the truffle extract, several things happen in an individual. Due to the increased testosterone levels, vitality, well-being, mood, mortality, sexuality (libido drive and performance), muscle (lean body mass and muscle), immunity, bone mass and repair, platelet aggregation, cognition, blood pressure, HDL cholesterol levels, and sleep quality are all improved. With regards to homeostasis, by increasing testosterone levels, abdominal fat is reduced (fat suppresses LH action and therefore testosterone production) and incidents of diabetes and cardiovascular disease are reduced.

The present invention also provides a method of preventing the onset of Alzheimer's disease in an individual by the individual smelling the composition (i.e. truffle extract) and inducing testosterone production in the individual and thereby increasing levels of testosterone in an individual. Alzheimer's disease is commonly found in the form of dementia (loss of memory and other intellectual functions), which is serious enough to interfere in daily life and presently does not have a cure. Available treatments focus on helping people maintain mental function, managing behavioral symptoms and slowing its development. 5.3 million people in the US have this disease. It is known that incidence of Alzheimer's disease increases when testosterone levels decrease. Pike Christian, et al., in "Androgens, aging and Alzheimer's disease" (2006) discussed new evidence that one consequence of testosterone depletion in men is an increased risk for the development of Alzheimer's disease (AD). Furthermore, two candidate mechanisms were discussed by which testosterone can affect AD pathogenesis. There are two possible mechanisms by which testosterone can affect AD pathogenesis. First, testosterone has been identified as an endogenous regulator of β-amyloid, a protein that abnormally accumulates in the AD brain and is implicated as a causal factor in the disease. Second, findings from several different paradigms indicate that testosterone has both neurotrophic and neuroprotective functions. These new findings support the clinical evaluation of androgen-based therapies for the prevention and treatment of AD. Therefore, the onset of Alzheimer's disease can be prevented or delayed by using the truffle extract of the present invention and increasing the levels of testosterone in the individual. The testosterone can then regulate β-amyloid and prevent accumulation in the brain.

The present invention provides a method of treating symptoms of menopause in women by a woman smelling the composition (i.e. truffle extract) and inducing the production of testosterone and thereby increasing levels of testosterone in a woman. Many women suffer from sweats, hot flushes, inability to sleep, lack of sex drive, and lack of vitality during menopause, and the truffle extract can prevent or lessen any or combinations of these symptoms. The olfaction of truffle can be used in addition to estrogen/progesterone treatment. It is generally known by doctors that testosterone is essentially in addition to estrogen/progesterone treatment.

The present invention also provides a method of treating andropause in men by a man smelling the composition (i.e. truffle extract) and inducing the production of testosterone and thereby increasing levels of testosterone in a man. Andropause is considered similar to menopause but occurring in men due to the loss of testosterone production, and causes the symptoms described above when lower levels of testosterone are produced.

There are several advantages to this method. The scent is a natural product, whereas current testosterone treatments use only synthetic testosterone. The scent of the truffle initiates an immediate response of increasing testosterone levels through the stimulation of testosterone production, not by adding testosterone to the body unlike other treatments. The composition is easy to apply because it is applied to the skin much like the application of perfume and can be done without a physician. Furthermore, the composition cannot be overdosed.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

In order to prepare a nutritional supplement grade tincture of organic mycelial biomass of *Tuber melanosporum*, organic truffles were grown on organic rye medium in the dark, in a truffle/mushroom farm with hydroponics in the United States. Truffles were harvested and anatomically confirmed to contain predominantly truffle mycelial biomass. Truffles thus grown were dried under sterile conditions and ground into a fine powder. Five (5) g. of the truffle powder thus produced was placed in a 100 ml beaker with a magnetic stirring bar on the bottom. One hundred (100) ml of 95% ethanol (USP Alcohol) was added to the truffle powder in the beaker. The beaker was then placed on a Corning stirrer/heat plate and the stirrer turned on, with stirring proceeding for thirty (30) minutes. The remaining powder in the beaker was allowed to settle to the bottom of the beaker, and the alcohol extract thus made was poured through a funnel lined with filter paper into a storage bottle. The clear aromatic brownish tincture thus produced was stored in a bottle at room temperature, after having been tightly capped.

An aliquot (1-2 drops) of the tincture was administered to human subjects as follows: ten human male subjects, ages 55-82, had saliva samples taken immediately upon awakening in the morning on the day prior to the start of the study, and the saliva samples were analyzed for testosterone level utilizing fluorescent microscopy. Then on a daily basis 1-2 drops of the tincture were administered by topical application to the upper lip of the subject, in the evening near the subject's normal bedtime, after which the subject did not wash or cover the skin thus topically treated. Administration once nightly continued for at least three days. Each subject had his morning saliva analyzed for testosterone 3-14 days after the onset of topical administration of the tincture; the increase in testosterone levels in picograms/ml is shown TABLE 1. All ten men 55+ in age had an increase in their testosterone levels, on average by 100% (see TABLE 1).

TABLE 1

| Name | Age | Pre (pg/ml) Baseline | Post (pg/ml) 3-14 days |
|---|---|---|---|
| MS | 82 | 64 | 87 |
| AC | 82 | 7 | 68 |
| Jim | 74 | 64 | 100 |
| BM | 73 | 61 | 69 |
| JM | 68 | 46 | 70 |
| JC | 65 | 26 | 47 |
| JP | 62 | 64 | 165 |
| TL | 60 | 68 | 74 |
| WH | 55 | 54 | 293 |
| TB | 55 | 56 | 82 |
| TB (2nd exposure - 5 mths later) | 55 | 52 | 275 |

EXAMPLE 2

Twelve women who were in menopause/post-menopausal stage used the olfaction of truffle extract. The above-described administration of the tincture to the upper lip was followed for olfaction therapy for a sequence of days, and it was reported that the administration removes common symptoms including hot flashes, sweating, inability to have a good night's sleep, anxiety, mood swings, general lack of vitality, and reduced libido. Overall, the benefits of the present therapy are multiple, including without limitation ease of use, virtual inability to overdose, and all the benefits and reduced toxicities of (in the preferred embodiment) a natural, organically produced product.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of treating andropause in a man including the steps of:
    the man smelling the truffle extract produced from alcohol extraction; and
    inducing testosterone production in the man.

2. The method of claim 1, further including the step of treating symptoms chosen from the group consisting of sweats, hot flushes, inability to sleep, lack of sex drive, lack of vitality, and combinations thereof.

3. The method of claim 1, wherein the truffle extract is derived from a truffle chosen from the group consisting of *Tuber magnatum, Tuber magnatum pico, Tuber borchii, Tuber melanosporum, Tuber aestivum, Tuber macrosporum, Tuber oregonense, Tuber gibbosum*, and *Tuber lyonii*.

* * * * *